(12) United States Patent
Bonda

(10) Patent No.: US 11,484,485 B2
(45) Date of Patent: Nov. 1, 2022

(54) PHOTOSTABILIZING COMPOUNDS, COMPOSITIONS, AND METHODS

(71) Applicant: ELC MANAGEMENT LLC, Melville, NY (US)

(72) Inventor: Craig Alan Bonda, Winfield, IL (US)

(73) Assignee: ELC MANAGEMENT LLC, Melville, NY (US)

( * ) Notice: Subject to any disclaimer, the term of this patent is extended or adjusted under 35 U.S.C. 154(b) by 130 days.

(21) Appl. No.: 17/254,231

(22) PCT Filed: Jun. 13, 2019

(86) PCT No.: PCT/US2019/037107
§ 371 (c)(1),
(2) Date: Dec. 18, 2020

(87) PCT Pub. No.: WO2019/245880
PCT Pub. Date: Dec. 26, 2019

(65) Prior Publication Data
US 2021/0267859 A1   Sep. 2, 2021

Related U.S. Application Data

(60) Provisional application No. 62/686,274, filed on Jun. 18, 2018.

(51) Int. Cl.
| A61K 8/40 | (2006.01) |
|---|---|
| A61K 8/49 | (2006.01) |
| A61K 8/67 | (2006.01) |
| A61Q 17/04 | (2006.01) |
| A61Q 19/08 | (2006.01) |

(52) U.S. Cl.
CPC ............ *A61K 8/40* (2013.01); *A61K 8/4953* (2013.01); *A61K 8/671* (2013.01); *A61Q 17/04* (2013.01); *A61Q 19/08* (2013.01); *A61K 2800/522* (2013.01)

(58) Field of Classification Search
None
See application file for complete search history.

(56) References Cited

U.S. PATENT DOCUMENTS

| 5,102,757 | A | 4/1992 | Akasaki et al. |
|---|---|---|---|
| 5,530,004 | A | 6/1996 | Clark et al. |
| 6,294,186 | B1 | 9/2001 | Beerse et al. |
| 6,919,473 | B2 | 7/2005 | Bonda et al. |
| 8,075,808 | B2 | 12/2011 | Bonda et al. |
| 8,088,901 | B2 | 1/2012 | Morishita et al. |
| 8,263,051 | B2 | 9/2012 | Bonda et al. |
| 8,268,294 | B2 | 9/2012 | Bonda et al. |
| 8,278,332 | B2 | 10/2012 | Bonda et al. |
| 8,329,148 | B1 | 12/2012 | Bonda et al. |
| 9,125,829 | B2 | 9/2015 | Bonda et al. |
| 9,145,383 | B2 | 9/2015 | Bonda et al. |
| 9,611,246 | B2 | 4/2017 | Bonda et al. |
| 9,765,051 | B2 | 9/2017 | Bonda et al. |
| 9,867,800 | B2 | 1/2018 | Bonda et al. |
| 9,926,289 | B2 | 3/2018 | Bonda et al. |
| 2003/0212077 | A1 | 11/2003 | Birnbaum |
| 2004/0062726 | A1 | 4/2004 | Bonda et al. |
| 2008/0254130 | A1 | 10/2008 | Gupta |
| 2009/0039323 | A1 | 2/2009 | Bonda et al. |
| 2013/0078202 | A1 | 3/2013 | Abdui-Malak et al. |
| 2014/0044654 | A1 | 2/2014 | Bonda et al. |
| 2014/0050681 | A1 | 2/2014 | Bonda et al. |
| 2017/0174992 | A1 | 6/2017 | Ootsuki |

FOREIGN PATENT DOCUMENTS

| CN | 105198875 | 12/2015 |
|---|---|---|
| CN | 106366036 | 2/2017 |
| JP | H02-097963 A | 4/1990 |
| JP | 2007-052063 | 3/2007 |
| JP | 2017-125009 A | 7/2017 |
| KR | 10-2011-0127026 | 11/2011 |
| WO | WO-2006/034968 | 4/2006 |
| WO | WO-2014/025370 | 2/2014 |
| WO | WO-2015/048550 | 4/2015 |
| WO | WO-2016/102069 | 6/2016 |

OTHER PUBLICATIONS

US 9,650,356 B2, 05/2017, Bonda et al. (withdrawn)
Dombeck, F. et al.; "Autoxidation of the antimicrobial alkaloid cleistopholine in solution"; Die Pharmazie—An International Journal of Pharmaceutical Sciences, 2006, vol. 61, No. 5, pp. 387-390.
Jockusch et al. "Photostabilization of endogenous porphyrins: excited state quenching by fused ring cyanoacrylates"; Photochemical & Photobiological Sciences; 2014; 13; pp. 1180-1184.
Nagaoka, S. I. et al.; "UV protection and singlet oxygen quenching activity of aloesaponarin I"; The Journal of Physical Chemistry B.. 2007, vol. 111, pp. 13116-13123.
PCT International Search Report; International Application No. PCT/US2019/037101; Completion Date: Oct. 18, 2019; dated Oct. 18, 2019; 18.11-1.
PCT International Search Report; International Application No. PCT/US2019/037104; Completion Date: Oct. 17, 2019; dated Oct. 18, 2019; 18.11-2.
PCT International Search Report; International Application No. PCT/US2019/037105; Completion Date: Oct. 17, 2019; dated Oct. 18, 2019; 18.11-3.

(Continued)

*Primary Examiner* — Nannette Holloman
(74) *Attorney, Agent, or Firm* — Yonggang Wu

(57) ABSTRACT

Photostabilizing compounds are provided. In particular, the photostabilizing compounds may be heterocyclic or homocyclic. Topical compositions comprising these compounds are also provided. In particular, these topical compositions may further comprise photoactive compounds. Methods for stabilizing photoactive compounds are also provided. These methods comprise mixing the photoactive compounds with photostabilizing compounds.

26 Claims, No Drawings

(56) References Cited

OTHER PUBLICATIONS

PCT International Search Report; International Application No. PCT/US2019/037107; Completion Date: Oct. 17, 2019; dated Oct. 18, 2019; 18.11-4.
PCT Written Opinion of the International Searching Authority; International Application No. PCT/US2019/037101; Completion Date: Oct. 18, 2019; dated Oct. 18, 2019; 18.11-1.
PCT Written Opinion of the International Searching Authority; International Application No. PCT/US2019/037104; Completion Date: Oct. 17, 2019; dated Oct. 18, 2019; 18.11-2.
PCT Written Opinion of the International Searching Authority; International Application No. PCT/US2019/037105; Completion Date: Oct. 17, 2019; dated Oct. 18, 2019; 18.11-3.
PCT Written Opinion of the International Searching Authority; International Application No. PCT/US2019/037107; Completion Date: Oct. 17, 2019; dated Oct. 18, 2019; 18.11-4.
Sako, K. et al.. Tetrahedron Letters, 2011, vol. 52., pp. 5865-5868.
Boldt P. et al.: "Quinones XVII [1] The First Anthraquinone-(2Q): 1,3,4,5,8-Pentamethyl-2,9-dihydro-2,9-anthracenedione", Journal Fur Praktische Chemie; vol. 339; Jan. 1, 1997; pp. 646-649.
Boldt Peter et al.: "Synthesis of 3,7-Di-tert-butyl-9-9,10-dimethyl-2,6-anthraquinone", Chemische Berichte; Jan. 1, 1987; pp. 497-500.
Boldt Peter: "Ein neues Chinonsystem: Derivative des amphi-Anthrachinons". Chem. Ber, vol. 100, No. 100; Jan. 1, 1967; pp. 1270-1280.
Chen Li-Jun et al.: "Chiral metallosupramolecular architectures", Chemical Society Reviews; vol. 46, No. 9; Jan. 1, 2017; pp. 2555-2576.
Quinn Jesse et al.: "New synthetic route to pyrimidol [4.5-g] quinazoline-4.9-diones"; Tetrahedron Letters; vol. 56, No. 17; Apr. 1, 2015; pp. 2280-2282.
Song Cheng-Li et al.: "Synthesis of Tetrachloro-azapentacene as an Ambipolar Organic Semiconductor with High and Balanced Carrier Mobilities"; Organic Letters; vol. 13, No. 11; Jun. 3, 2011; pp. 2880-2883.
Utley et al.: "Electroorganic reactions, part 47. The cathodic hydrogenation of azafluoren-9-ylidine probases", Electrochimica Acta. Elsevier, Amsterdam, NL; vol. 42, No. 13; Jan. 1, 1997; pp. 2109-2115.
"Aerobic Dehydrogenative Heck Reaction of Ferrocene with a Pd(OA)2/4,5-Diazafluoren-9-one Catalyst"; Piotrowickz et al.; Organometallics; 2013; vol. 32, No. 20; pp. 5709-5757.
"Electroorganic reactions, part 47. The cathodic hydrogenation of azafluoren-9-ylidine probases"; Utley et al; Electrochimica Acta; 1997; vol. 42, No. 13-14; pp. 2019-2115.
"New Dicarboxylic Acid Bipyridine Ligand for Ruthenium Polypyridyl Sensitization of TiO2": Inorganic Chemistry; 2012; vol. 51; No. 7, pp. 3981-3988.
Chemistry of Heterocyclic Compounds (Khimiya Geterotsiklicheskikh Soedinenii); vol. 24, No. 9; 1988; pp. 1024-1027.
Journal of Electroanalytical Chemistry and Interfaciai Electrochemistry; "Electro-Organic Reactions"; "Part 34. Kinetic Basicities of Some Electrogenerated Organic Dianions and the Competition Between Protonation and Reproportionation"; Sim K. Ling-Chung, et al.; 1988; vol. 250, No. 2; pp. 373-384.
Olenyuk et al.: "Design and Study of Synthetic Chiral Nanoscopic Assemblies. Preparation and Characterization of Optically Active Hybrid, Iodonium-Transition-Metal and All-Transition-Metal Macrocyclic Molecular Squares", Journal of the American Chemical Society, 118, pp. 8221-8230, Sep. 4, 1996.
Stang et al., "Directed Self-Assembly of Chiral, Optically Active Macrocyclic Tetranuclear Molecular Squares", Angewandte Chemie International Edition, 35, pp. 732-736, Apr. 19, 1996.
Tetrahedron Letters; "New synthetic route to pyrimido[4,5-g]quinazoline-4,9-diones"; 2015; vol. 56; No. 17; pp. 2280-2282.
Chemistry Europe; "Cross-Conjugated π-Scaffolding with Pendant N-Heterocyclic Metal-Binding Sites"; Djawed Nauroozi et al.; vol. 2017; Issue21; pp. 3101-3106 https://chemistry-europe.onlinelibrary.wiley.com/doi/abs/10.1002/ejoc.201700294.
Journals of Materials of Chemistry C; "4,5-Diazafluorene co-oligomers as electron-deficient light-emitting materials and selective fluorescence sensors for mercury(ii) cations"; Gosh et al.; Issue 14, 2018 https://www.sciencedirect.com/science/article/abs/pii/S0040403911014924.
Science Direct; "Synthesis and redox properties of p-conjugated 4,5-diazafluorene derivatives incorporating 9-cyanomethylene moiety as an electron acceptor"; Tetrahedron Letters; Sako et al.; vol. 52, Issue 44, Nov. 2, 2011, pp. 5865-5868 https://www.sciencedirect.com/science/article/abs/pii/S0040403911014924.
Supplementary European Search Report; EP Application No. 19822738.1; Completion Date: Sep. 3, 2021; 18.11-1.
Supplementary European Search Report; EP Application No. 19822604.5; Completion Date: Aug. 27, 2021; 18.11-2.
Supplementary European Search Report; EP Application No. 19823549.1; Completion Date: Aug. 27, 2021; 18.11-3.
Supplementary European Search Report; EP Application No. 19823594.7; Completion Date: Jul. 13, 2021; 18.11-4.
Choi Jun Rye et al.: "Two-photon-induced excited-state intramolecular proton transfer process in 1-hydroxyanthraquinone", Chemical Physics Letters; vol. 385, No. 5-6; Feb. 1, 2004; pp. 384-388.
Chowdhury Nargis Sultana et al.: "Cytotoxic Naphthoquinone and Azaanthraquinone Derivatives from an Endophytic Fusarium solani"; Journal of Natural Products; vol. 80, No. 4; Mar. 3, 2017; pp. 1173-1177.
Cui Hui et al.: "Alkaloids from the mangrove endophytic fungusDiaporthe phaseolorumSKS019", Bioorganic & Medicinal Chemistry Letters, ELSEVIER, Amsterdam, NL; vol. 27, No. 4; Jan. 13, 2017; pp. 803-807.
Heuer et al.: "New Dicarboxylic Acid Bipyridine Ligand for Ruthenium Polypyridyl Sensitization of TiO 2"; Inorganic Chemistry; vol. 51. No. 7; Apr. 2, 2012; pp. 3981-3988.
Neuwahl Frederik V. R. et al.: "Ultrafast proton transfer in the S1 state of 1-chloroacetylaminoanthraquinone"; Physical Chemistry Chemical Physics, vol. 3, No. 7; Jan. 1, 2001; pp. 1277-1283.
Prostakov et al.: "Condensation of 4-azafluorenone and 9-phenacylidene-4-azafluorene with acetophenone. Synthesis of 3?-oxo-spiro-[4-azafluorene-9,1?-indane]", Chemistry of Heterocyclic Compounds; vol. 24, No. 9; Sep. 1, 1988; pp. 1024-1027.

PHOTOSTABILIZING COMPOUNDS, COMPOSITIONS, AND METHODS

RELATED APPLICATIONS

This application claims priority from provisional patent application Ser. No. 62/686,274 filed on Jun. 18, 2018.

TECHNICAL FIELD

The disclosure is in the field of compounds that stabilize chemical sunscreens or other compounds that are photoactive, and related compositions and methods.

BACKGROUND OF THE DISCLOSURE

Photoactive compounds are widely used. For example, sunscreens are photoactive compounds. The most widely used UVA and UVB filters in sunscreens are Avobenzone (butyl methoxydibenzoylmethane) and Octoxinate (ethylhexyl methoxycinnamate). While effective in blocking UVA and UVB rays respectively, upon exposure to UV light both Avobenzone and Octinoxate are subject to degradation. Upon exposure to UV light Octinoxate will sometimes form dimers with other Octinoxate molecules. These dimers no longer absorb UVB and UVB efficacy is lost. Octinoxate will also react with the double bond of the dominant form of Avobenzone resulting in the formation of cyclobutane which then forms ring opening structures. The result is loss of UVA efficacy.

Retinoids are also photoactive compounds. Upon exposure to UV light, retinoids are subject to photoreactions, such as photoisomerization, photopolymerization, photooxidation, and photodegradation. The resulted photodecomposition products do not have the same level of biological activities. The result is loss of biological efficacy.

Photostabilizers such as N-cyanodiphenylacrylates such as Octocrylene (2-Cyano-3,3-Diphenyl Acrylic Acid, 2-Ethylhexyl Ester) are known to inhibit the UV-induced photo degradation of Avobenzone. When Avobenzone absorbs a photon of UV light its electron enters a triplet energy state, which can lead to the photo-degradation of the Avobenzone. Octocrylene is able to accept the triplet excited state energy and return the Avobenzone to its original unexcited state. However, when Octoxinate is present, it sometimes will accept the triplet excited state energy from Avobenzone and then react with the double bond found in the dominant form of Avobenzone. Accordingly, Octocrylene is sometimes, but not always, effective for its intended purpose.

The problem of solving the instability of photoactive compounds is critical. Sunscreens like Avobenzone and Octinoxate are widely used. Particularly, Avobenzone is one of the only UVA sunscreens approved for global use in sunscreen products. Also, retinoids are highly desired due to their biological benefits and efficacies. Particularly, retinol is an important regulator in epidermal cell growth, normal cell differentiation, and cell maintenance.

The disclosure is directed to photostabilizing compounds, compositions comprising those photostabilizing compounds, and related methods for stabilizing photoactive compounds that may include chemical sunscreens, such as Avobenzone or Octinoxate in particular, as well as other unstable compounds such as retinol.

SUMMARY OF THE DISCLOSURE

The disclosure is directed to photostabilizing compounds having a structure according to the formula selected from the group consisting of:

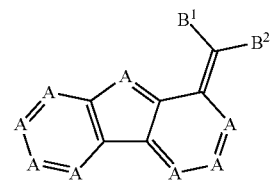

Formula I

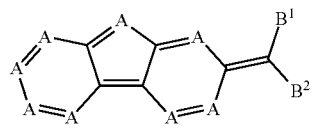

Formula II

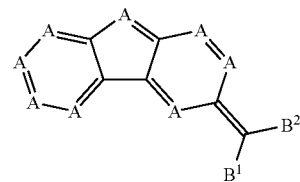

Formula III

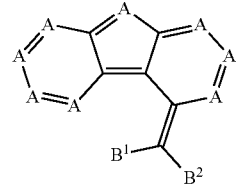

Formula IV

In one embodiment, each A is independently selected from the group consisting of $CR^1$ and N.

In one aspect, $R^1$ is selected from the group consisting of H, OH, a straight or branched chain alkyl group having from about 1 to about 20 carbon atoms, an alkoxy group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms. Preferably, IV is selected from H, a straight or branched chain alkyl group having from about 1 to about 20 carbon atoms, an alkoxy group having from about 1 to about 20 carbon atoms. More preferably, IV is selected from H, a straight or branched chain alkyl group having from about 1 to about 20 carbon atoms. Most preferably, IV is selected from the group consisting of H, and a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl.

In one alternative embodiment, each A is independently selected from the group consisting of CH and N.

In one embodiment, no more than four As are N. In one aspect, at least one A is N. In one aspect, no A is N.

In one alternative embodiment, each of $B^1$ and $B^2$ is independently selected from the group consisting of CN, $C(=O)OR^2$. In one aspect, $B^1$ and $B^2$ are not both CN. In one aspect, at least one of $B^1$ and $B^2$ is $C(=O)OR^2$.

In one alternative aspect, $R^2$ selected from the group consisting of H, a straight or branched chain alkyl group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms. Preferably, $R^2$ is a straight or branched chain alkyl group having from about 1 to about 20 carbon atoms.

More preferably, $R^2$ is a straight or branched chain alkyl group having at least 8, no more than 12 carbon atoms. Most Preferably, $R^2$ is a straight or branched chain alkyl group having 8 carbon atoms.

In one embodiment, the photostabilizing compound has a structure according to Formula I.

In one embodiment, the photostabilizing compound has a structure according to Formula II.

In one embodiment, the photostabilizing compound has a structure according to Formula III.

In one embodiment, the photostabilizing compound has a structure according to Formula IV.

In one embodiment, the photostabilizing compound is selected from the group consisting of Compound 1-5.

The disclosure is also directed to compositions comprising at least one compound having a structure according to the formula selected from the group consisting of Formula I, II, III, and IV.

In one embodiment, the composition comprises the photostabilizing compound present in amount ranging from 0.01 to 25% by weight of the total composition. Preferably, the photostabilizing compound is present in the composition in amount ranging from 0.05 to 15% by weight of the total composition. More preferably, the photostabilizing compound is present in the composition in amount ranging from 0.1 to 5% by weight of the total composition.

In one embodiment, the composition further comprises at least one photoactive compound. Preferably, the photoactive compound is selected from the group consisting of a retinoid, a sunscreen, or mixture thereof.

In one aspect, the photoactive compound is a retinoid. Preferably, the retinoid is retinol.

In one aspect, the retinoid is present in amount ranging from about 0.0001 to about 20% by weight of the total composition. Preferably, the retinoid is present in amount ranging from about 0.001 to about 10% by weight of the total composition. More preferably, the retinoid is present in amount ranging from about 0.01 to about 8% by weight of the total composition. Most preferably, the retinoid is present in amount ranging from about 0.05 to about 5% by weight of the total composition.

In one aspect, the photoactive compound is a sunscreen. Preferably, the sunscreen is selected from the group consisting of a UVA chemical sunscreen, a UVB chemical sunscreen, a physical sunscreen, and mixture thereof.

In one alternative aspect, the sunscreen is a UVA chemical sunscreen. Preferably, the UVA chemical sunscreen is selected from a group consisting of a dibenzoylmethane compound and a dicamphor sulfonic acid derivative. More preferably, the UVA chemical sunscreen is selected from a group consisting of dibenzoylmethane compounds. Examples of the dibenzoylmethane compounds include, but not limit to, 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane. Most preferably, the UVA chemical sunscreen is Avobenzone.

In one alternative aspect, the UVA chemical sunscreen is present in amount ranging from about 0.001 to about 20% by weight of the total composition. Preferably, the UVA chemical sunscreen is present in amount ranging from about 0.005 to about 5% by weight of the total composition. More preferably, UVA chemical sunscreen is present in amount ranging from about 0.005 to about 3% by weight of the total composition.

In one alternative aspect, the UVA chemical sunscreen is Avobenzone and is present at not greater than about 3% by weight of the total composition.

In one alternative aspect, the sunscreen is a UVB chemical sunscreen. Preferably, the UVB chemical sunscreen is selected from the group consisting of an alpha-cyano-beta, beta-diphenyl acrylic acid ester, a benzylidene camphor derivative, a cinnamate derivative, a benzophenone derivative, a menthyl salicylate derivative, an amino benzoic acid derivative, a salicylate derivative, and an ester of 2-phenyl ethanol and benzoic acid. More preferably, the UVB chemical sunscreen is selected from the group consisting of Octocrylene, 4-methylbenzylidene camphor, Octinoxate, Cinoxate, Benzophenone 3, Sulisobenzone, Sulisobenzone Sodium, Homosalate, ethyl hexyl dimethyl PABA, ethyldihydroxypropyl PABA, octyl salicylate, TEA-salicylate, DEA-salicylate, phenyethyl benzoate. More preferably, the UVB chemical sunscreen is selected from the group consisting of Octocrylene, 4-methylbenzylidene camphor, Octinoxate, Benzophenone 3, Homosalate, ethyl hexyl dimethyl PABA, octyl salicylate. Most preferably, the UVB chemical sunscreen is Octinoxate.

In one alternative aspect, the UVB chemical sunscreen is present in amount ranging from about 0.001 to about 45% by weight of the total composition. Preferably, the UVB chemical sunscreen is present in amount ranging from about 0.005 to about 40% by weight of the total composition. More preferably, UVA chemical sunscreen is present in amount ranging from about 0.01 to about 35% by weight of the total composition.

In one aspect, the composition is a sunscreen composition. Preferably, the sunscreen composition has a SPF value ranging from about 1 to about 50. More preferably, the sunscreen composition has a SPF value ranging from about 2 to about 45. Most preferably, the sunscreen composition has a SPF value ranging from about 5 to about 30.

The disclosure is also directed to methods for stabilizing a photoactive compound, comprising mixing the photoactive compound with at least one photostabilizing compound having a structure according to the formula selected from the group consisting of Formula I, II, III, and IV.

In one embodiment, the photoactive compound is selected from a group consisting of Avobenzone, Octinoxate, retinol, or mixtures thereof against photo degradation due to exposure to UV light.

DETAILED DESCRIPTION

Photostabilizing compounds are highly desired. In some embodiments, the present disclosure relates to compounds having the capability to stabilize photoactive compounds.

Each electron in one molecule has two possible spin states. When two electrons of a molecule are at the same molecular orbit and have opposite spin states, these two electrons form an electron pair. When all electrons of a molecule are paired, this molecule is at a singlet state because the electronic energy levels of this molecule would not split when exposed into a magnetic field. When a molecule has only one unpaired electron, this molecule is at a doublet state because the electronic energy levels of this molecule may split into two levels when exposed into a magnetic field. When a molecule has two unpaired electrons whose spin states are parallel to each other, this molecule is at a triplet state because the electronic energy levels of this molecule may split into three levels when exposed into a magnetic field.

In some embodiments, all electrons of the photoactive compound are paired at the ground state.

In some embodiments, upon exposure to visible light and/or UV light, the photon absorption of the photoactive compound may cause electron excitation. In some alternative embodiments, upon excitation, an electron of one electron pair may be promoted from the lower energy ground state to a higher energy excited state. The electron pair may be unpaired, with one electron at the excited state and another at the ground state. In one aspect, the excited electron may not change the spin orientation, and keeps the spin orientation opposite to the spin orientation of the other unpaired electron. This excited molecule is at a singlet excited state. In another aspect, the excited electron changes its spin orientation, which becomes parallel to the spin orientation of the other unpaired electron. This excited molecule is at a triplet excited state.

In some embodiments, the photoactive compounds may become less stable upon being excited, subject to photochemical reactions that are mostly irreversible. After undergoing these irreversible reactions, the photoactive compounds generally lose their desired properties and efficacies. Because many photoactive compounds are widely used in the industry due to their great properties and efficacies, it is critical to find a way to stabilize photoactive compounds.

In some embodiments, the photostabilizing compounds may stabilize photoactive compounds. In one aspect, the photostabilizing compounds may be capable of directly or indirectly assisting the energy transfer from the excited photoactive compounds. In one alternative aspect, the excited photoactive compounds may be less likely to undergo photochemical reactions as they may more likely get back to their more stable states (i.e., the ground state) before undergoing photochemical reactions due to the co-existing photostabilizing compounds. By lowering the possibility that the photoactive compounds undergo irreversible photochemical reactions after being excited, the photostabilizing compounds may effectively stabilize photoactive compounds.

A. The Compounds

How photostabilizing compounds assist the energy transfer from the excited photoactive compounds is not well understood.

In some embodiments, the present disclosure relates to photostabilizing compounds. In one alternative embodiment, the photostabilizing compound is heterocyclic. A heterocyclic compound is one that contains at least a ring made up of more than one kind of atom.

In one aspect, the heteroatom of the heterocyclic compound may be nitrogen, oxygen, and/or sulfur. In a compound, a heteroatom is the atom in a ring that is not a carbon atom. Preferably, the heteroatom of the heterocyclic compound may be nitrogen.

Nitrogen as the heteroatom may affect the properties of compounds in various ways. Nitrogen is more electronegative than carbon is. That is, nitrogen has the higher tendency to attract a bonding pair of electrons than the tendency that carbon has. Also, Nitrogen has a lone pair of electrons that may not form a bond with other atoms.

In one aspect, the nitrogen's lone pair may be on a p orbital perpendicular to the ring. In this case, nitrogen may act as an electron donor to π orbitals of the system. In another aspect, the nitrogen's lone pair may be on a sp² hybrid orbit and lie outside the heterocyclic ring. In this case, nitrogen may act as an electron acceptor of the 6 orbitals of the heterocyclic system because it is more electron negative than carbon. The molecular electronic structure of the heterocyclic compound may change dramatically when the number of the nitrogen atom(s) and the position(s) of nitrogen atom(s) change. The photophysical and photochemical properties of the heterocyclic compound may change according to the changes of its molecular electronic structure. By carefully choosing the number of nitrogen atom(s) on the ring and the position(s) of nitrogen atom(s), desired photophysical and photochemical properties of the compounds may be achieved.

In one alternative embodiment, the photostabilizing compound is homocyclic. A homocyclic compound is one that does not contain a ring made up of more than one kind of atom.

In some embodiments, the photostabilizing compounds may be selected from constitutional isomers. Constitutional isomers are molecules with the same molecular formula having different bonding patterns and atomic organization. Each constitutional isomer may have its unique photophysical and photochemical properties due to its unique molecular electronic structure.

In some preferred embodiments, the photostabilizing compound may be conjugated.

In one aspect, the photostabilizing compound may be aromatic, non-aromatic, or anti-aromatic. Preferably, the compound may be aromatic.

In some embodiments, the disclosure is related to photostabilizing compounds having the structure according to the following formulas:

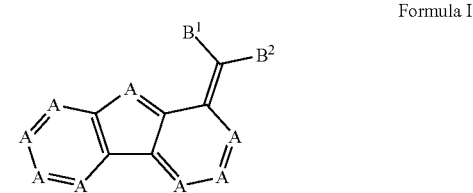

Formula I

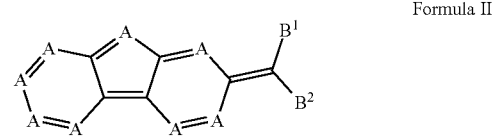

Formula II

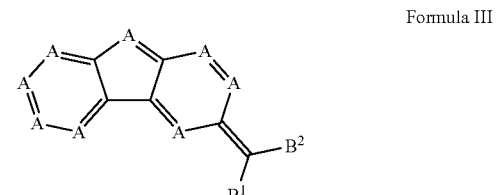

Formula III

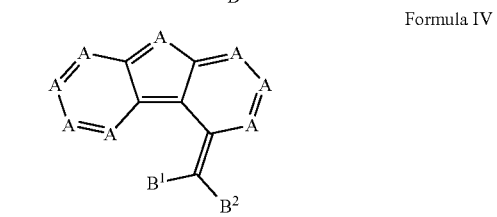

Formula IV

In one embodiment, each A is independently selected from the group consisting of $CR^1$ and N.

In one aspect, $R^1$ is selected from the group consisting of:
(i) H;
(ii) OH;
(iii) a straight or branched chain alkyl group having from about 1 to about 20 carbon atoms, preferably having from about 1 to about 10 carbon atoms, more preferably having from about 1 to about 6 carbon atoms; in one alternative aspect, the alkyl group is a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl;
(iv) an alkoxy group having from about 1 to about 20 carbon atoms, preferably having from about 1 to about 12 carbon atoms, more preferably having from about 1 to about 6 carbon atoms, most preferably the alkoxy group is selected from the group consisting of methoxy, ethoxy, propoxy, butoxy;
(v) an alkenyl group having from about 2 to about 20 carbon atoms, preferably having from about 2 to about 12 carbon atoms, more preferably having from about 2 to about 6 carbon atoms, most preferably the alkenyl group is selected from the group consisting of vinyl, allyl, cyclopentenyl, hexenyl;
(vi) an alkynyl group having from about 2 to about 20 carbon atoms, preferably having from about 2 to about 12 carbon atoms, more preferably having from about 2 to about 6 carbon atoms;
(vii) an aryl group having from about 6 to about 20 carbon atoms, preferably having from about 6 to about 14 carbon atoms, more preferably having from about 6 to about 12 carbon atoms.

In one preferred aspect, $R^1$ is selected from H; and a straight or branched chain alkyl group having from about 1 to about 20 carbon atoms, preferably having from about 1 to about 10 carbon atoms, more preferably having from about 1 to about 6 carbon atoms; in one alternative aspect, the alkyl group is a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl.

In one alternative embodiment, each A is independently selected from the group consisting of CH and N.

In one embodiment, no more than four As are N. In one aspect, at least one A is N. In one aspect, no A is N.

In one embodiment, each of $B^1$ and $B^2$ is independently selected from the group consisting of CN, C(=O)OR². In one aspect, $B^1$ and $B^2$ are not both CN. In one aspect, at least one of $B^1$ and $B^2$ is C(=O)OR².

In one aspect, $R^2$ is selected from the group consisting of
(i) H;
(ii) a straight or branched chain alkyl group having from about 1 to about 20 carbon atoms, preferably having from about 8 to about 12 carbon atoms, more preferably having about 8 carbon atoms; in one alternative aspect, the alkyl group is a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl, preferably a straight or branched octyl group;
(iii) an alkenyl group having from about 2 to about 20 carbon atoms, preferably having from about 2 to about 12 carbon atoms, more preferably having from about 2 to about 6 carbon atoms, most preferably the alkenyl group is selected from the group consisting of vinyl, allyl, cyclopentenyl, hexenyl;
(iv) an alkynyl group having from about 2 to about 20 carbon atoms, preferably having from about 2 to about 12 carbon atoms, more preferably having from about 2 to about 6 carbon atoms;
(v) an aryl group having from about 6 to about 20 carbon atoms, preferably having from about 6 to about 14 carbon atoms, more preferably having from about 6 to about 12 carbon atoms.

In one preferred aspect, $R^2$ is selected from H; and a straight or branched chain alkyl group having from about 1 to about 20 carbon atoms, preferably having from about 1 to about 10 carbon atoms; in one alternative aspect, the alkyl group is a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl, preferably a straight or branched octyl group.

By carefully selecting R', the photophysical and photochemical properties of the compounds may be further optimized.

By carefully selecting $R^1$ and $R^2$, the hydrophilicity and/or lipophilicity of the compounds may be optimized. The hydrophilicity and/or lipophilicity of the compounds may play an important role in formulating the compositions comprising the compounds.

Specific, non-limiting examples of compounds are provided:

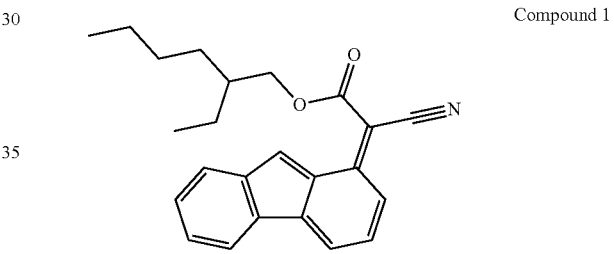

Compound 1

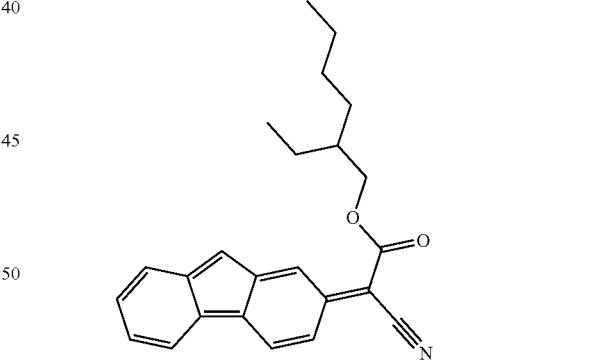

Compound 2

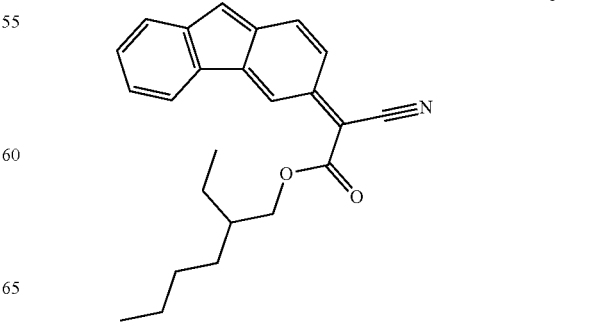

Compound 3

-continued

Compound 4

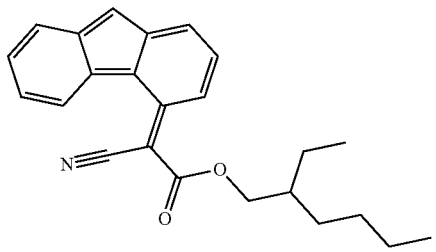

Compound 5

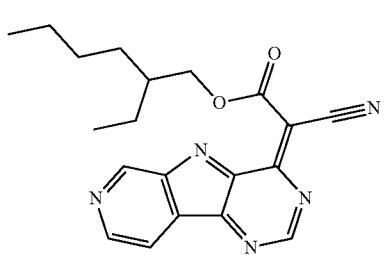

B. The Compositions

In some embodiments, the compositions of the disclosure may be topical compositions. In one aspect, the topical compositions may be in the form of solids, liquids, or gels. In one aspect, the topical compositions may be aqueous based or anhydrous. Aqueous based compositions may be in the form of emulsions, solutions, or dispersions.

In some embodiments, the compositions comprise at least one compound having a structure according to the formula selected from the group consisting of Formula I, II, III, and IV. In one aspect, the compound having a structure according to the formula selected from the group consisting of Formula I, II, III, and IV may be present in amounts ranging from about 0.01 to about 25%, preferably about 0.05 to about 15%, more preferably from about 0.1 to about 5% by weight of the total composition.

In some embodiments, the topical compositions may further comprise certain esters of 2-phenyl ethanol and benzoic acid. One example is phenethyl benzoate, which is sold under the tradename X-Tend 226®, by Ashland.

In some embodiments, the topical compositions may further contain oils, waxes, thickening agents, vitamins, preservatives, antioxidants, botanical extracts, chemical or physical sunscreens or other ingredients.

In some preferred embodiments, the compositions comprise at least one photoactive compound.

In one aspect, the photoactive compounds are retinoids and derivatives thereof. Preferably, the compositions comprise retinyl palmitate, retinol, retinoic acid, and/or Vitamin A in the form of beta carotene.

In one aspect, the retinoid is present in amount ranging from about 0.0001 to about 20% by weight of the total composition. Preferably, the retinoid is present in amount ranging from about 0.001 to about 10% by weight of the total composition. More preferably, the retinoid is present in amount ranging from about 0.01 to about 8% by weight of the total composition. Most preferably, the retinoid is present in amount ranging from about 0.05 to about 5% by weight of the total composition.

In one aspect, the photoactive compounds is sunscreen. Such sunscreens include chemical UVA or UVB sunscreens or physical sunscreens.

1. UVA Chemical Sunscreens

If desired, the composition may comprise one or more UVA sunscreens. The term "UVA sunscreen" means a chemical compound that blocks UV radiation in the wavelength range of about 320 to 400 nm. Preferred UVA sunscreens are dibenzoylmethane compounds having the general formula:

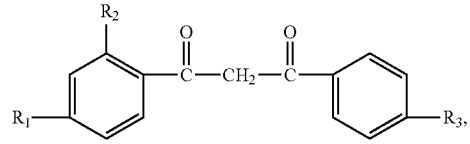

wherein $R_1$ is H, OR and NRR wherein each R is independently H, $C_{1-20}$ straight or branched chain alkyl; $R_2$ is H or OH; and $R_3$ is H, $C_{1-20}$ straight or branched chain alkyl.

Preferred is where $R_1$ is OR where R is a $C_{1-20}$ straight or branched alkyl, preferably methyl; $R_2$ is H; and $R_3$ is a $C_{1-20}$ straight or branched chain alkyl, more preferably, butyl.

Examples of suitable UVA sunscreen compounds of this general formula include 4-methyldibenzoylmethane, 2-methyldibenzoylmethane, 4-isopropyldibenzoylmethane, 4-tert-butyldibenzoylmethane, 2,4-dimethyldibenzoylmethane, 2,5-dimethyldibenzoylmethane, 4,4'diisopropylbenzoylmethane, 4-tert-butyl-4'-methoxydibenzoylmethane, 4,4'-diisopropylbenzoylmethane, 2-methyl-5-isopropyl-4'-methoxydibenzoymethane, 2-methyl-5-tert-butyl-4'-methoxydibenzoylmethane, and so on. Particularly preferred is 4-tert-butyl-4'-methoxydibenzoylmethane, also referred to as Avobenzone. Avobenzone is commercially available from Givaudan-Roure or DSM under the trademark Parsol 1789, and Merck & Co. under the tradename Eusolex 9020, and Symrise under the tradename Neo Heliopan 357, and has a structure according to the following formula:

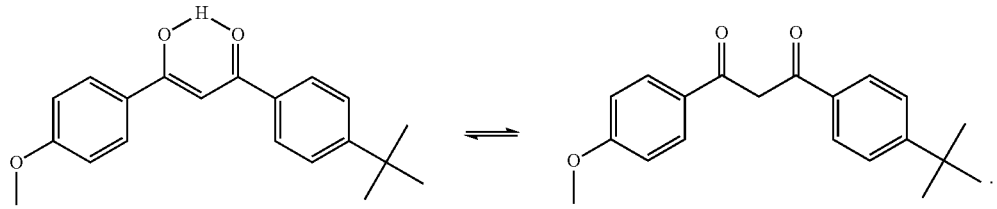

In the preferred embodiment of the disclosure, the composition comprises at least one dibenzoylmethane sunscreen, preferably Avobenzone.

Other types of UVA sunscreens include dicamphor sulfonic acid derivatives, such as ecamsule, a sunscreen sold by Chimex under the trade name Mexoryl SX, which is terephthalylidene dicamphor sulfonic acid, having the structure according to the following formula:

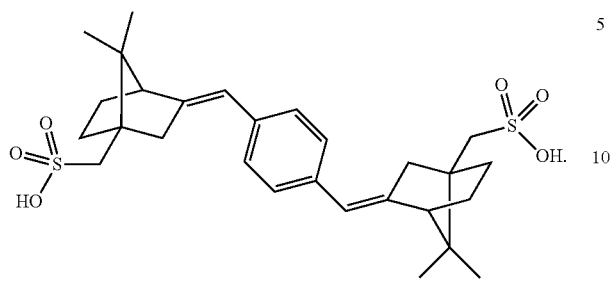

The composition may contain from about 0.001-20%, preferably about 0.005-5%, more preferably about 0.005-3% by weight of the composition of UVA sunscreen. In the preferred embodiment of the disclosure the UVA sunscreen is Avobenzone, and it is present at not greater than about 3% by weight of the total composition.

2. UVB Chemical Sunscreens

The term "UVB sunscreen" means a compound that blocks UV radiation in the wavelength range of from about 290 to 320 nm. A variety of UVB chemical sunscreens exist including alpha-cyano-beta, beta-diphenyl acrylic acid esters as set forth in U.S. Pat. No. 3,215,724, which is hereby incorporated by reference in its entirety. One particular example of an alpha-cyano-beta, beta-diphenyl acrylic acid ester is Octocrylene, which is 2-ethylhexyl 2-cyano-3,3-diphenylacrylate. In certain cases the composition may contain no more than about 110% by weight of the total composition of octocrylene. Suitable amounts range from about 0.001-10% by weight. Octocrylene may be purchased from BASF under the tradename Uvinul N-539, from DSM under tradename Parsol 340, and from Symrise under the tradename Neo Heliopan 303, and has a structure according to the following formula:

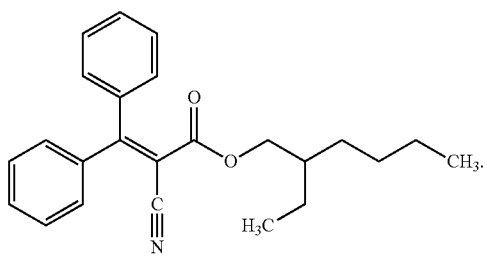 [SMILES: CCCCC(CC)COC(=O)C(C#N)=C(c1ccccc1)c1ccccc1]

Other suitable sunscreens include benzylidene camphor derivatives as set forth in U.S. Pat. No. 3,781,417, which is hereby incorporated by reference in its entirety. Such benzylidene camphor derivatives have the general formula:

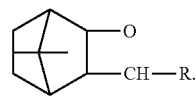

wherein R is p-tolyl or styryl, preferably styryl. Particularly preferred is 4-methylbenzylidene camphor, which is a lipid soluble UVB sunscreen compound sold under the tradename Eusolex 6300 by Merck, and Neo Heliopan MBC by Symrise, and Parsol 5000 by DSM, having a structure according to the following formula:

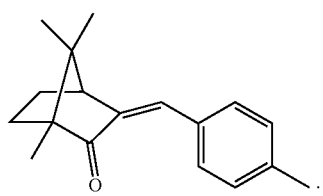 [SMILES: Cc1ccc(/C=C2\C(=O)C3(C)CCC2C3(C)C)cc1]

Also suitable are cinnamate derivatives having the general formula:

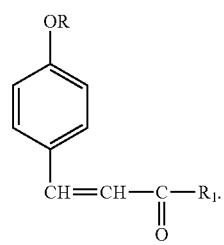

wherein R and $R_1$ are each independently a $C_{1-20}$ straight or branched chain alkyl. Preferred is where R is methyl and $R_1$ is a branched chain $C_{1-10}$, preferably $C_8$ alkyl. The preferred compound is ethylhexyl methoxycinnamate, also referred to as Octinoxate or octyl methoxycinnamate. Octinoxate may be purchased from Givaudan Corporation and DSM under the tradename Parsol MCX, or BASF under the tradename Uvinul MC 80, or Symrise under the tradename Neo Heliopan AV, or Ashland under the tradename Escalol 557, having a structure according to the following structure:

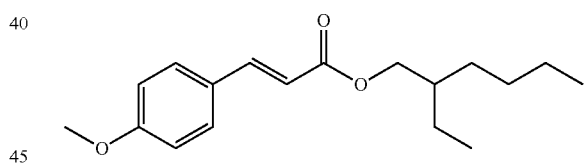

Also suitable are mono-, di-, and triethanolamine derivatives of such methoxy cinnamates including diethanolamine methoxycinnamate. Cinoxate, the aromatic ether derivative of the above compound is also acceptable. If present, the Cinoxate should be found at no more than about 3% by weight of the total composition.

Also suitable as UVB screening agents are various benzophenone derivatives having the general formula:

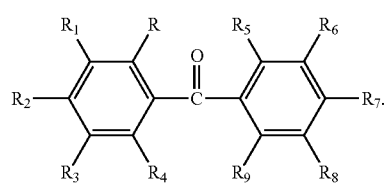

wherein R through $R_9$ are each independently H, OH, $NaO_3S$, $SO_3H$, $SO_3Na$, Cl, R'', OR'' where R'' is $C_{1-20}$ straight or branched chain alkyl Examples of such compounds include Benzophenone 1, 2, 3, 4, 5, 6, 7, 8, 9, 10, 11, and 12. Particularly preferred is where the benzophenone derivative is Benzophenone 3 (also referred to as Oxybenzone), Benzophenone 4 (also referred to as Sulisobenzone), Benzophenone 5 (Sulisobenzone Sodium), and the like. Most preferred is Benzophenone 3, which may be purchased under the tradename Uvinul M-40 and NeoHeliopan BB, having the structure according to the following formula:

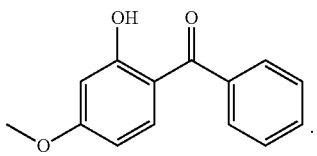 [SMILES: COc1ccc(C(=O)c2ccccc2)c(O)c1]

Also suitable are certain menthyl salicylate derivatives having the general formula:

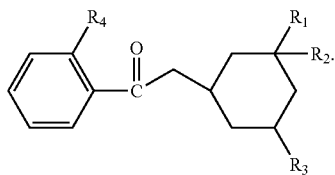

wherein $R_1$, $R_2$, $R_3$, and $R_4$ are each independently H, OH, $NH_2$, or $C_{1-20}$ straight or branched chain alkyl. Particularly preferred is where $R_1$, $R_2$, and $R_3$ are methyl and $R_4$ is hydroxyl or $NH_2$, the compound having the name homomenthyl salicylate (also known as Homosalate) or menthyl anthranilate. Menthyl anthranilate is commercially available from Haarmann & Reimer under the tradename Heliopan. Homosalate is available commercially from Merck under the tradename Eusolex HMS, and from Symrise under the tradename Neo Heliopan HMS, and from DSM under the tradename Parsol HMS, having the structure according to the following formula:

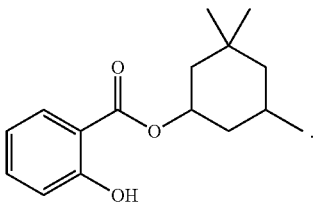 [SMILES: CC1CC(OC(=O)c2ccccc2O)CC(C)(C)C1]

If present, the Homosalate should be present at no more than about 15% by weight of the total composition.

Various amino benzoic acid derivatives are suitable UVB absorbers including those having the general formula:

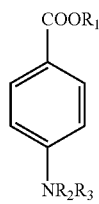

wherein $R_1$, $R_2$, and $R_3$ are each independently H, $C_{1-20}$ straight or branched chain alkyl which may be substituted with one or more hydroxy groups. Particularly preferred is wherein $R_1$ is H or $C_{1-8}$ straight or branched alkyl, and $R_2$ and $R_3$ are H, or $C_{1-8}$ straight or branched chain alkyl. Particularly preferred are PABA, ethyl hexyl dimethyl PABA (Padimate O), ethyldihydroxypropyl PABA, and the like. If present Padimate O should be found at no more than about 8% by weight of the total composition.

Salicylate derivatives are also acceptable UVB absorbers. Such compounds have the general formula: wherein R is a straight or branched chain alkyl, including derivatives of the above compound formed from mono-, di-, or triethanolamines. Particular preferred are octyl salicylate, TEA-salicylate, DEA-salicylate, and mixtures thereof. Octyl salicylate has the INCI name Ethylhexyl salicylate, and may be purchased from Ashland under the tradename Escalol 587, and Merck under the tradename Eusolex OS, and has the structure according to the following formula:

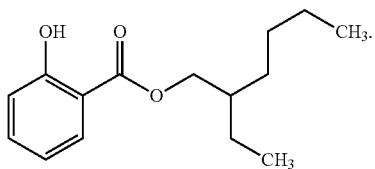 [SMILES: CCCCC(CC)COC(=O)c1ccccc1O]

Generally, the amount of the UVB chemical sunscreen present may range from about 0.001-45%, preferably about 0.005-40%, more preferably about 0.01-35% by weight of the total composition.

In one preferred embodiment, the sunscreen may be Avobenzone and/or Octinoxate. It may also be desirable to include one or more other sunscreens in the compositions of the disclosure.

In one preferred embodiment, the composition may be an oil in water emulsion comprising 5-85% water, 1-40% oil, 0.1-10% Homosalate, 0.1-5% Avobenzone, If desired, the compositions of the disclosure may be formulated to have a certain SPF (sun protective factor) values ranging from about 1-100, preferably about 4-80, most preferably about 15-60. Calculation of SPF values is well known in the art.

3. Other Ingredients:

The topical composition may contain the following ingredients:

Oils

Suitable oils include silicones, esters, vegetable oils, synthetic oils, including but not limited to those set forth herein. The oils may be volatile or nonvolatile, and are preferably in the form of a pourable liquid at room temperature. If present, the oils may range from about 0.5 to 85%, preferably from about 1-75%, more preferably from about 5-65% by weight of the total composition.

Cyclic and linear volatile silicones are available from various commercial sources including Dow Chemical Corporation and Momentive (formerly General Electric Silicones). The Dow Chemical linear volatile silicones are sold under the trade names Dowsil and Xiameter 244, 245, 344, and 200 fluids. These fluids include hexamethyldisiloxane (viscosity 0.65 centistokes (abbreviated cst)), octamethyltrisiloxane (1.0 cst), decamethyltetrasiloxane (1.5 cst), dodecamethylpentasiloxane (2 cst) and mixtures thereof, with all viscosity measurements being at 25° C.

Suitable branched volatile silicones include alkyl trimethicones such as methyl trimethicone, a branched volatile silicone having the general formula:

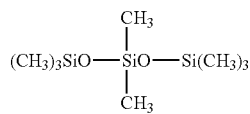

Methyl trimethicone may be purchased from Shin-Etsu Silicones under the trade name TMF-1.5, having a viscosity of 1.5 centistokes at 25° C.

Also suitable are various straight or branched chain paraffinic hydrocarbons having 5, 6, 7, 8, 9, 10, 11, 12, 13, 14, 15, 16, 17, 18, 19, or 20 carbon atoms, more preferably 8 to 16 carbon atoms. Suitable hydrocarbons include pentane, hexane, heptane, decane, dodecane, tetradecane, tridecane, and $C_{8-20}$ isoparaffins. Suitable $C_{12}$ isoparaffins are manufactured by Permethyl Corporation under the tradename Permethyl 99A. Various $C_{16}$ isoparaffins commercially available, such as isohexadecane (having the tradename Permethyl R), are also suitable.

Also suitable are esters formed by the reaction of a carboxylic acid and an alcohol. The alcohol and the carboxylic acids may both have fatty ($C_{6-30}$) chains. Examples include hexyl laurate, butyl isostearate, hexadecyl isostearate, cetyl palmitate, isostearyl neopentanoate, stearyl heptanoate, isostearyl isononanoate, stearyl lactate, stearyl octanoate, stearyl stearate, isononyl isononanoate, and so on.

The ester may also be in the dimer or trimer form. Examples of such esters include diisotearyl malate, neopentyl glycol dioctanoate, dibutyl sebacate, dicetearyl dimer dilinoleate, dicetyl adipate, diisocetyl adipate, diisononyl adipate, diisostearyl dimer dilinoleate, diisostearyl fumarate, diisostearyl malate, dioctyl malate, and so on.

Examples of other types of esters include those from arachidonic, citric, or behenic acids, such as triarachidin, tributyl citrate, triisostearyl citrate, tri $C_{12-13}$ alkyl citrate, tricaprylin, tricaprylyl citrate, tridecyl behenate, trioctyldodecyl citrate, tridecyl behenate; or tridecyl cocoate, tridecyl isononanoate, and so on.

Synthetic or naturally occurring glyceryl esters of fatty acids, or triglycerides, are also suitable for use in the compositions. Both vegetable and animal sources may be used. Examples of such oils include castor oil, lanolin oil, $C_{10-18}$ triglycerides, caprylic/capric/triglycerides, sweet almond oil, apricot kernel oil, sesame oil, camelina sativa oil, tamanu seed oil, coconut oil, corn oil, cottonseed oil, linseed oil, ink oil, olive oil, palm oil, illipe butter, rapeseed oil, soybean oil, grapeseed oil, sunflower seed oil, walnut oil, and the like.

Also suitable are synthetic or semi-synthetic glyceryl esters, such as fatty acid mono-, di-, and triglycerides which are natural fats or oils that have been modified, for example, mono-, di- or triesters of polyols such as glycerin. In an example, a fatty ($C_{12-22}$) carboxylic acid is reacted with one or more repeating glyceryl groups. glyceryl stearate, diglyceryl diiosostearate, polyglyceryl-3 isostearate, polyglyceryl-4 isostearate, polyglyceryl-6 ricinoleate, glyceryl dioleate, glyceryl diisostearate, glyceryl tetraisostearate, glyceryl trioctanoate, diglyceryl distearate, glyceryl linoleate, glyceryl myristate, glyceryl isostearate, PEG castor oils, PEG glyceryl oleates, PEG glyceryl stearates, PEG glyceryl tallowates, and so on.

Nonvolatile silicone oils, both water soluble and water insoluble, are also suitable for use in the composition. Such silicones preferably have a viscosity ranging from about greater than 5 to 800,000 cst, preferably 20 to 200,000 cst at 25° C. Suitable water insoluble silicones include amine functional silicones such as amodimethicone. Examples include dimethicone, phenyl dimethicone, diphenyl dimethicone, phenyl trimethicone, or trimethylsiloxyphenyl dimethicone. Other examples include alkyl dimethicones such as cetyl dimethicone, stearyl dimethcone, behenyl dimethicone, and the like.

Surfactants

The composition may contain one or more surfactants, especially if in the emulsion form. However, such surfactants may be used if the compositions are anhydrous also, and will assist in dispersing ingredients that have polarity, for example pigments. Such surfactants may be silicone or organic based. The surfactants will aid in the formation of stable emulsions of either the water-in-oil or oil-in-water form. If present, the surfactant may range from about 0.001 to 30%, preferably from about 0.005 to 25%, more preferably from about 0.1 to 20% by weight of the total composition.

Silicone surfactants may be generically referred to as dimethicone copolyol or alkyl dimethicone copolyol. In some cases the number of repeating ethylene oxide or propylene oxide units in the polymer are also specified, such as a dimethicone copolyol that is also referred to as PEG-15/PPG-10 dimethicone, which refers to a dimethicone having substituents containing 15 ethylene glycol units and 10 propylene glycol units on the siloxane backbone. It is also possible for one or more of the methyl groups in the above general structure to be substituted with a longer chain alkyl (e.g. ethyl, propyl, butyl, etc.) or an ether such as methyl ether, ethyl ether, propyl ether, butyl ether, and the like.

Examples of silicone surfactants are those sold by Dow Silicones under the tradename Dowsil 3225C Formulation Aid having the CTFA name cyclotetrasiloxane (and) cyclopentasiloxane (and) PEG/PPG-18 dimethicone; or 5225C Formulation Aid, having the CTFA name cyclopentasiloxane (and) PEG/PPG-18/18 dimethicone; or Dowsil 190 Surfactant having the CTFA name PEG/PPG-18/18 dimethicone; or Dowsil 193 Fluid, Dowsil 5200 having the CTFA name lauryl PEG/PPG-18/18 methicone; or Abil EM 90 having the CTFA name cetyl PEG/PPG-14/14 dimethicone sold by Goldschmidt; or Abil EM 97 having the CTFA name bis-cetyl PEG/PPG-14/14 dimethicone sold by Goldschmidt; or Abil WE 09 having the CTFA name cetyl PEG/PPG-10/1 dimethicone in a mixture also containing polyglyceryl-4 isostearate and hexyl laurate; or KF-6011 sold by Shin-Etsu Silicones having the CTFA name PEG-11 methyl ether dimethicone; KF-6012 sold by Shin-Etsu Silicones having the CTFA name PEG/PPG-20/22 butyl ether dimethicone; or KF-6013 sold by Shin-Etsu Silicones having the CTFA name PEG-9 dimethicone; or KF-6015 sold by Shin-Etsu Silicones having the CTFA name PEG-3 dimethicone; or KF-6016 sold by Shin-Etsu Silicones having the CTFA name PEG-9 methyl ether dimethicone; or KF-6017 sold by Shin-Etsu Silicones having the CTFA name PEG-10 dimethicone; or KF-6038 sold by Shin-Etsu Silicones having the CTFA name lauryl PEG-9 polydimethylsiloxyethyl dimethicone.

Also suitable are various types of crosslinked silicone surfactants that are often referred to as emulsifying elastomers that contain at least one hydrophilic moiety such as polyoxyalkylenated groups. Polyoxyalkylenated silicone elastomers that may be used in at least one embodiment of the disclosure include those sold by Shin-Etsu Silicones under the names KSG-21, KSG-20, KSG-30, KSG-31, KSG-32, KSG-33; KSG-210 which is dimethicone/PEG-10/15 crosspolymer dispersed in dimethicone; KSG-310 which is PEG-15 lauryl dimethicone crosspolymer; KSG-320 which is PEG-15 lauryl dimethicone crosspolymer dispersed in isododecane; KSG-330 (the former dispersed in triethylhexanoin), KSG-340 which is a mixture of PEG-10 lauryl dimethicone crosspolymer and PEG-15 lauryl dimethicone crosspolymer.

Also suitable are polyglycerolated silicone elastomers like those disclosed in PCT/WO 2004/024798, which is hereby incorporated by reference in its entirety. Such elastomers include Shin-Etsu's KSG series, such as KSG-710 which is dimethicone/polyglycerin-3 crosspolymer dispersed in dimethicone; or lauryl dimethicone/polyglycerin-3 crosspolymer dispersed in a variety of solvent such as isododecane, dimethicone, triethylhexanoin, sold under the Shin-Etsu tradenames KSG-810, KSG-820, KSG-830, or KSG-840. Also suitable are silicones sold by Dow Silicones under the tradenames 9010 and DC9011.

The composition may comprise one or more nonionic organic surfactants. Suitable nonionic surfactants include alkoxylated alcohols, or ethers, formed by the reaction of an alcohol with an alkylene oxide, usually ethylene or propylene oxide. Preferably the alcohol is either a fatty alcohol having 6 to 30 carbon atoms. Examples of such ingredients include Steareth 2-100, which is formed by the reaction of stearyl alcohol and ethylene oxide and the number of ethylene oxide units ranges from 2 to 100; Beheneth 5-30 which is formed by the reaction of behenyl alcohol and ethylene oxide where the number of repeating ethylene oxide units is 5 to 30; Ceteareth 2-100, formed by the reaction of a mixture of cetyl and stearyl alcohol with ethylene oxide, where the number of repeating ethylene oxide units in the molecule is 2 to 100; Ceteth 1-45 which is formed by the reaction of cetyl alcohol and ethylene oxide, and the number of repeating ethylene oxide units is 1 to 45, and so on. All recitations of units include all whole integers between the range.

Other alkoxylated alcohols are formed by the reaction of fatty acids and mono-, di- or polyhydric alcohols with an alkylene oxide. For example, the reaction products of $C_{6-30}$ fatty carboxylic acids and polyhydric alcohols which are monosaccharides such as glucose, galactose, methyl glucose, and the like, with an alkoxylated alcohol. Examples include polymeric alkylene glycols reacted with glyceryl fatty acid esters such as PEG glyceryl oleates, PEG glyceryl stearate; or PEG polyhydroxyalkanotes such as PEG dipolyhydroxystearate wherein the number of repeating ethylene glycol units ranges from 3 to 1000.

Other suitable nonionic surfactants include alkoxylated sorbitan and alkoxylated sorbitan derivatives. For example, alkoxylation, in particular ethoxylation of sorbitan provides polyalkoxylated sorbitan derivatives. Esterification of polyalkoxylated sorbitan provides sorbitan esters such as the polysorbates. For example, the polyalkyoxylated sorbitan can be esterified with $C_{6-30}$, preferably $C_{12-22}$ fatty acids. Examples of such ingredients include Polysorbates 20-85, sorbitan oleate, sorbitan sesquioleate, sorbitan palmitate, sorbitan sesquiisostearate, sorbitan stearate, and so on.

Humectants

It may also be desirable to include one or more humectants in the composition. If present, such humectants may range from about 0.001 to 25%, preferably from about 0.005 to 20%, more preferably from about 0.1 to 15% by weight of the total composition. Examples of suitable humectants include glycols, sugars, and the like. Suitable glycols are in monomeric or polymeric form and include polyethylene and polypropylene glycols such as PEG 4-200, which are polyethylene glycols having from 4 to 200 repeating ethylene oxide units; as well as $C_{1-6}$ alkylene glycols such as propylene glycol, butylene glycol, pentylene glycol, and the like. Suitable sugars, some of which are also polyhydric alcohols, are also suitable humectants. Examples of such sugars include glucose, fructose, honey, hydrogenated honey, inositol, maltose, mannitol, maltitol, sorbitol, sucrose, xylitol, xylose, and so on. Also suitable is urea. Preferably, the humectants used in the composition of the disclosure are $C_{1-6}$, preferably $C_{2-4}$ alkylene glycols, most particularly butylene glycol.

Botanical Extracts

It may be desirable to include one or more botanical extracts in the compositions. If so, suggested ranges are from about 0.0001 to 10%, preferably about 0.0005 to 8%, more preferably about 0.001 to 5% by weight of the total composition. Suitable botanical extracts include extracts from plants (herbs, roots, flowers, fruits, seeds) such as flowers, fruits, vegetables, and so on, including yeast ferment extract, *Padina pavonica* extract, thermus thermophilis ferment extract, camelina sativa seed oil, boswellia serrata extract, olive extract, *Aribodopsis thaliana* extract, *Acacia dealbata* extract, *Acer saccharinum* (sugar maple), acidopholus, acorus, aesculus, agaricus, agave, agrimonia, algae, aloe, citrus, brassica, cinnamon, orange, apple, blueberry, cranberry, peach, pear, lemon, lime, pea, seaweed, caffeine, green tea, chamomile, willowbark, mulberry, poppy, and those set forth on pages 1646 through 1660 of the CTFA Cosmetic Ingredient Handbook, Eighth Edition, Volume 2. Further specific examples include, but are not limited to, *Glycyrrhiza glabra, Salix nigra, Macrocycstis pyrifera, Pyrus malus, Saxifraga sarmentosa, Vitis vinifera, Morus nigra, Scutellaria baicalensis, Anthemis nobilis, Salvia sclarea, Rosmarinus officianalis, Citrus medica limonum, Panax ginseng, Siegesbeckia orientalis, Fructus mume, Ascophyllum nodosum*, Bifida Ferment lysate, *Glycine soja* extract, *Beta vulgaris, Haberlea rhodopensis, Polygonum cuspidatum, Citrus aurantium dulcis, Vitis vinifera, Selaginella tamariscina, Humulus lupulus, Citrus reticulata* Peel, *Punica granatum, Asparagopsis, Curcuma longa, Menyanthes trifoliata, Helianthus annuus*, Hordeum vulgare, *Cucumis sativus, Evernia prunastri, Evernia furfuracea*, and mixtures thereof.

Particulate Materials

The compositions of the disclosure may contain particulate materials in the form of pigments, inert particulates, or mixtures thereof. If present, suggested ranges are from about 0.01-75%, preferably about 0.5-70%, more preferably about 0.1-65% by weight of the total composition. In the case where the composition may comprise mixtures of pigments and powders, suitable ranges include about 0.01-75% pigment and 0.1-75% powder, such weights by weight of the total composition.

The particulate matter may be colored or non-colored powders. Suitable non-pigmented powders include bismuth oxychloride, titanated mica, fumed silica, spherical silica, polymethylmethacrylate, micronized teflon, boron nitride, acrylate copolymers, aluminum silicate, aluminum starch octenylsuccinate, bentonite, calcium silicate, cellulose, chalk, corn starch, diatomaceous earth, fuller's earth, glyceryl starch, hectorite, hydrated silica, kaolin, magnesium aluminum silicate, magnesium trisilicate, maltodextrin, montmorillonite, microcrystalline cellulose, rice starch, silica, talc, mica, titanium dioxide, zinc laurate, zinc myristate, zinc rosinate, alumina, attapulgite, calcium carbonate, calcium silicate, dextran, kaolin, nylon, silica silylate, silk powder, sericite, soy flour, tin oxide, titanium hydroxide, trimagnesium phosphate, walnut shell powder, or mixtures thereof. The above mentioned powders may be surface treated with lecithin, amino acids, mineral oil, silicone, or various other agents either alone or in combination, which coat the powder surface and render the particles more lipophilic in nature.

Suitable pigments are organic or inorganic. Organic pigments are generally various aromatic types including azo, indigoid, triphenylmethane, anthroquinone, and xanthine dyes which are designated as D&C and FD&C blues, browns, greens, oranges, reds, yellows, etc. Organic pigments generally consist of insoluble metallic salts of certified color additives, referred to as the Lakes. Inorganic pigments include iron oxides, ultramarines, chromium, chromium hydroxide colors, and mixtures thereof. Iron oxides of red, blue, yellow, brown, black, and mixtures thereof are suitable.

Vitamins and Antioxidants

The compositions of the disclosure may contain vitamins and/or coenzymes, as well as antioxidants. If so, 0.001-10%, preferably 0.01-8%, more preferably 0.05-5% by weight of the total composition is suggested. Suitable vitamins include ascorbic acid and derivatives thereof such as ascorbyl palmitate, tetrahexydecyl ascorbate, and so on; the B vitamins such as thiamine, riboflavin, pyridoxin, and so on, as well as coenzymes such as thiamine pyrophoshate, flavin adenin dinucleotide, folic acid, pyridoxal phosphate, tetrahydrofolic acid, and so on. Also suitable is Vitamin E and derivatives thereof such as Vitamin E acetate, nicotinate, or other esters thereof. In addition, Vitamins D and K are suitable.

C. The Methods

In some embodiments, the disclosure is related to methods for stabilizing photoactive compounds, the methods comprise mixing a least one photoactive compound with at least one photostabilizing compound having a structure according to the formula selected from the group consisting of Formula I, II, III, and IV.

In one aspect, the methods for stabilizing retinoids and derivatives thereof comprise mixing a least one retinoid and/or derivatives thereof with at least one photostabilizing compound having a structure according to the formula selected from the group consisting of Formula I, II, III, and IV.

In one aspect, the methods for stabilizing chemical sunscreens comprise mixing a least one chemical sunscreen with at least one photostabilizing compound having a structure according to the formula selected from the group consisting of Formula I, II, III, and IV.

The disclosure will be further described in connection with the following examples which are set forth for the purposes of illustration only.

EXPERIMENTAL

Compound Examples

Example 1

Synthesis of Compound 1

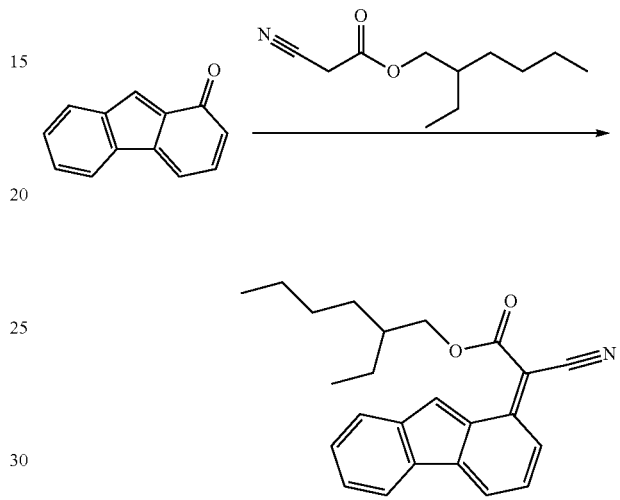

1-Fluorenone (4.0 gm, 22.1 mmol) and toluene (40 mL) are mixed in a clean 250 mL 2 neck round bottom flask equipped with Dean-Stark condenser and nitrogen inlet. 2-ethylhexyl cyanoacetate (4.4 gm, 22.3 mmol), ammonium acetate (153 mg, 1.99 mmol), and acetic acid (2.8 mL) are added sequentially at 25-30° C. The reaction mixture is refluxed for approximately 18 hours at 100-115° C. The water is periodically removed from Dean-Stark condenser during the reaction. The reaction is monitored by TLC (30% ethyl acetate/hexane). After the complete consumption of 1-fluorenone by TLC, the reaction mixture is cooled to room temperature. The toluene layer is washed with water (2×25 mL) followed by saturated sodium bicarbonate solution (25 mL) and again with water (25 mL). The organic layer is evaporated under reduced pressure at 45-50° C. to obtain crude product as pale brown semisolid. The crude product is purified by column chromatography by eluting with 10-15% ethyl acetate in hexane to afford pure product.

Example 2

Synthesis of Compound 2

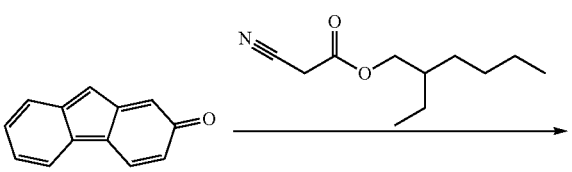

-continued

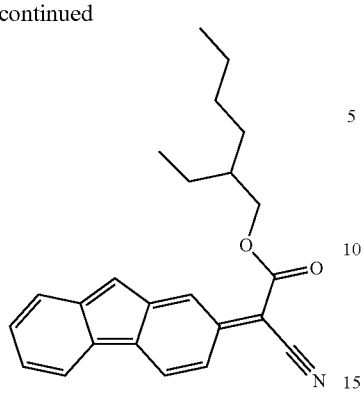

2-Fluorenone (4.0 gm, 22.1 mmol) and toluene (40 mL) are mixed in a clean 250 mL 2 neck round bottom flask equipped with Dean-Stark condenser and nitrogen inlet. 2-ethylhexyl cyanoacetate (4.4 gm, 22.3 mmol), ammonium acetate (153 mg, 1.99 mmol), and acetic acid (2.8 mL) are added sequentially at 25-30° C. The reaction mixture is refluxed for approximately 18 hours at 100-115° C. The water is periodically removed from Dean-Stark condenser during the reaction. The reaction is monitored by TLC (30% ethyl acetate/hexane). After the complete consumption of 2-fluorenone by TLC, the reaction mixture is cooled to room temperature. The toluene layer is washed with water (2×25 mL) followed by saturated sodium bicarbonate solution (25 mL) and again with water (25 mL). The organic layer is evaporated under reduced pressure at 45-50° C. to obtain crude product as pale brown semisolid. The crude product is purified by column chromatography by eluting with 10-15% ethyl acetate in hexane to afford pure product.

Example 3

Synthesis of Compound 3

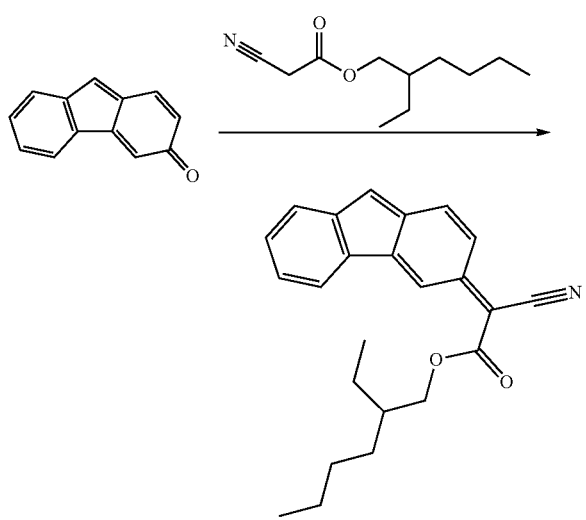

3-Fluorenone (4.0 gm, 22.1 mmol) and toluene (40 mL) are mixed in a clean 250 mL 2 neck round bottom flask equipped with Dean-Stark condenser and nitrogen inlet. 2-ethylhexyl cyanoacetate (4.4 gm, 22.3 mmol), ammonium acetate (153 mg, 1.99 mmol), and acetic acid (2.8 mL) are added sequentially at 25-30° C. The reaction mixture is refluxed for approximately 18 hours at 100-115° C. The water is periodically removed from Dean-Stark condenser during the reaction. The reaction is monitored by TLC (30% ethyl acetate/hexane). After the complete consumption of 3-fluorenone by TLC, the reaction mixture is cooled to room temperature. The toluene layer is washed with water (2×25 mL) followed by saturated sodium bicarbonate solution (25 mL) and again with water (25 mL). The organic layer is evaporated under reduced pressure at 45-50° C. to obtain crude product as pale brown semisolid. The crude product is purified by column chromatography by eluting with 10-15% ethyl acetate in hexane to afford pure product.

Example 4

Synthesis of Compound 4

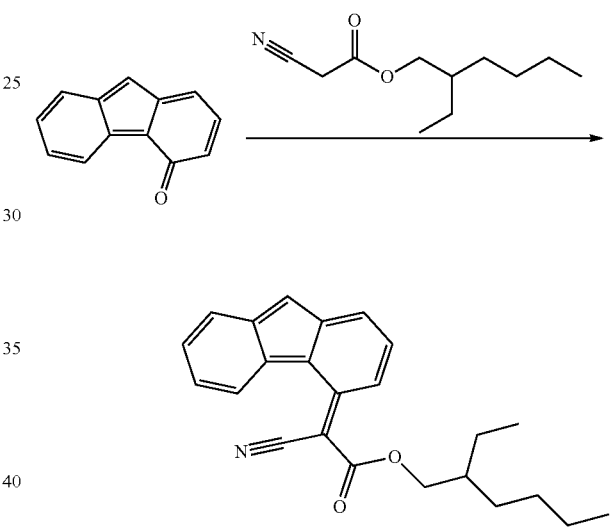

4-Fluorenone (4.0 gm, 22.1 mmol) and toluene (40 mL) are mixed in a clean 250 mL 2 neck round bottom flask equipped with Dean-Stark condenser and nitrogen inlet. 2-ethylhexylcyano acetate (4.4 gm, 22.3 mmol), ammonium acetate (153 mg, 1.99 mmol), and acetic acid (2.8 mL) are added sequentially at 25-30° C. The reaction mixture is refluxed for approximately 18 hours at 100-115° C. The water is periodically removed from Dean-Stark condenser during the reaction. The reaction is monitored by TLC (30% ethyl acetate/hexane). After the complete consumption of 4-fluorenone by TLC, the reaction mixture is cooled to room temperature. The toluene layer is washed with water (2×25 mL) followed by saturated sodium bicarbonate solution (25 mL) and again with water (25 mL). The organic layer is evaporated under reduced pressure at 45-50° C. to obtain crude product as pale brown semisolid. The crude product is purified by column chromatography by eluting with 10-15% ethyl acetate in hexane to afford pure product.

Example 5

Synthesis of Compound 5

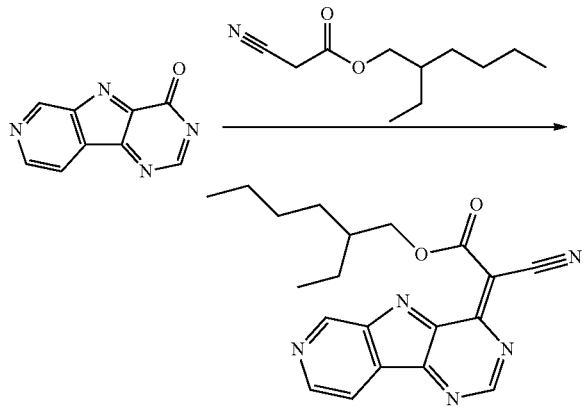

2,4,7,9-Tetraaza-1-fluorenone (4.0 gm, 22.1 mmol) and toluene (40 mL) are mixed in a clean 250 mL 2 neck round bottom flask equipped with Dean-Stark condenser and nitrogen inlet. 2-ethylhexylcyano acetate (4.4 gm, 22.3 mmol), ammonium acetate (153 mg, 1.99 mmol), and acetic acid (2.8 mL) are added sequentially at 25-30° C. The reaction mixture is refluxed for approximately 18 hours at 100-115° C. The water is periodically removed from Dean-Stark condenser during the reaction. The reaction is monitored by TLC (30% ethyl acetate/hexane). After the complete consumption of 2,4,7,9-tetraaza-1-fluorenone by TLC, the reaction mixture is cooled to room temperature. The toluene layer is washed with water (2×25 mL) followed by saturated sodium bicarbonate solution (25 mL) and again with water (25 mL). The organic layer is evaporated under reduced pressure at 45-50° C. to obtain crude product as pale brown semisolid. The crude product is purified by column chromatography by eluting with 10-15% ethyl acetate in hexane to afford pure product.

Composition Examples

Example 6

An anti-aging cream is prepared as follows:

| Ingredient | Wt % |
| --- | --- |
| Water | QS100 |
| Shea butter | 6.00 |
| Caprylic/capric/myristic/stearic triglyceride | 5.50 |
| Methyl trimethicone | 5.00 |
| Di-C12-15 alkyl fumarate | 4.00 |
| Dimethicone/polysilicone-11 | 4.00 |
| Butylene glycol | 3.00 |
| Steareth-2 | 2.30 |
| Glyceryl stearate | 1.50 |
| Pentylene glycol | 1.50 |
| Stearyl alcohol | 1.50 |
| Steareth-21 | 1.20 |
| Glycerin | 1.00 |
| Phenoxyethanol | 0.50 |
| Acrylamide/sodium acryloyldimethyltaurate copolymer/water/isohexadecane/polysorbate 80 | 0.50 |
| Fragrance | 0.40 |
| Carbomer | 0.35 |
| Water/sodium hydroxide | 0.28 |
| Cholesterol | 0.20 |
| Linoleic acid | 0.20 |
| Caffeine | 0.20 |
| Dimethicone | 0.20 |
| Sodium dehydroacetate | 0.10 |
| Tocopherol acetate | 0.10 |
| Compound 1 | 0.50 |

The composition is prepared by separately mixing the oil phase ingredients including the Compound 1. The water phase ingredients are combined and emulsified with the oil phase ingredients to form an emulsion.

Example 7

A formula with stabilized retinol is prepared as follows:

| Ingredient | Wt % |
| --- | --- |
| Water | QS100 |
| Butylene glycol | 1.60 |
| Sodium bisulfite | 0.02 |
| Caffeine | 0.20 |
| Silica | 0.20 |
| Caprylic/capric triglyceride | 3.17 |
| Dimethicone | 3.00 |
| Cetearyl alcohol | 2.00 |
| Tocopheryl acetate | 0.50 |
| Tocopherol | 0.20 |
| Disodium EDTA | 0.10 |
| Sodium hyaluronate | 0.10 |
| Cholesterol | 0.20 |
| Arachidyl alcohol | 1.37 |
| Polysorbate 60 | 0.03 |
| Behenyl alcohol | 0.75 |
| Sodium hydroxide | 0.07 |
| Hydroxyethylcellulose | 0.30 |
| Retinol | 0.30 |
| Stearyl dimethicone | 2.25 |
| Caprylyl glycol | 0.32 |
| Glycerin | 2.50 |
| Shea butter | 2.80 |
| Sorbitan olivate | 0.80 |
| Sorbitan isostearate | 0.03 |
| Cetearyl olivate | 1.20 |
| Arachidyl glucoside | 0.38 |
| PEG-12 dimethicone/PPG-20 crosspolymer | 1.60 |
| Compound 1 | 0.15 |

The composition is prepared by separately combining the water phase and oil phase with the Compound 1. The phases are mixed to emulsify and form a lotion.

Example 8

A sunscreen composition containing Compound 1 is prepared as follows:

| Phase | Ingredient | Wt % |
| --- | --- | --- |
| A | Deionized water | QS100 |
| B | Glycerin | 2.50 |
| B | Triethanolamine | 0.60 |
| B | Disodium EDTA | 0.10 |
| C | Compound 1 | 2.00 |
| C | Dimethicone (2 cs) | 2.00 |
| C | Glyceryl stearate/PEG 100 stearate | 2.50 |
| C | Beeswax | 1.00 |

-continued

| Phase | Ingredient | Wt % |
|---|---|---|
| D | Avobenzone | 3.00 |
| D | Homosalate | 10.00 |
| D | Octisalate | 5.00 |
| D | Octocrylene | 4.00 |
| F | Dimethicone/Acrylates dimethicone copolymer | 2.50 |
| F | Trimethylsiloxysilicate/dimethicone | 2.50 |
| G | Ammonium/Acryloyldimethyltaurate copolymer | 0.50 |
| H | Caprylyl glycol/phenoxyethanol/hexylene glycol | 1.00 |

The Phase A ingredients are charged into a main kettle. Phase B ingredients are added and propeller mixed at medium/high speed until homogeneous. The batch is then heated to a temperature of 67-70° C. In an auxiliary kettle the Phase C ingredients are heated to 65-70° C. and mixed with a propeller at medium speed. The Phase D ingredients are added and mixing at medium speed continued until uniform. The heat is lowered to 63° C. and the Phase E ingredients are added into the vortex with propeller mixing until dispersed. Phases C, D, and E are added into the main batch (A+B) while mixing at high speed. The composition is homogenized at 2000 rpm for 15-20 minutes. When the batch is emulsified and homogeneous, propeller mixing is continued and pre-mixed Phase F ingredients are added and mixed until uniform while cooling the batch to room temperature. Phases G and H are then added and mixed until uniform. The batch is cooled to room temperature.

OTHER EMBODIMENTS

While the invention has been described in connection with the preferred embodiment, it is not intended to limit the scope of the invention to the particular form set forth but, on the contrary, it is intended to cover such alternatives, modifications, and equivalents as may be included within the spirit and scope of the invention as defined by the appended claims. Therefore, other embodiments, including those can be easily modified by a person skilled in the art from the present disclosure, are also within the claims.

The invention claimed is:

1. A photostabilizing compound having a structure according to the formula selected from the group consisting of:

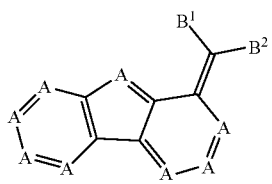
Formula I

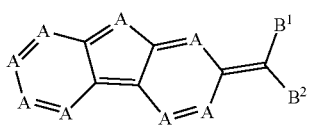
Formula II

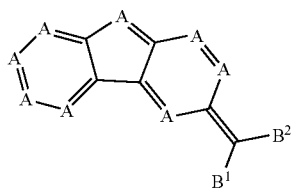
Formula III

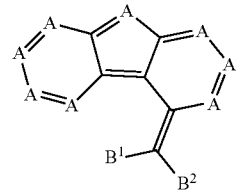
Formula IV wherein each A is independently selected from the group consisting of $CR^1$ and N;

wherein $R^1$ is selected from the group consisting of H, OH, a straight or branched chain alkyl group having from about 1 to about 20 carbon atoms, an alkoxy group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms;

wherein no more than four As are N;

wherein each of $B^1$ and $B^2$ is independently selected from the group consisting of CN, C(=O)$OR^2$, with the proviso that $B^1$ and $B^2$ are not both CN;

wherein $R^2$ is selected from the group consisting of H, an alkyl group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms.

2. The photostabilizing compound of claim 1, wherein the photostabilizing compound is heterocyclic.

3. The photostabilizing compound of claim 1, wherein the photostabilizing compound is homocyclic.

4. The photostabilizing compound of claim 1, wherein the photostabilizing compound having a structure according to Formula I.

5. The photostabilizing compound of claim 1, wherein the photostabilizing compound having a structure according to Formula II.

6. The photostabilizing compound of claim 1, wherein the compound having a structure according to Formula III.

7. The photostabilizing compound of claim 1, wherein the photostabilizing compound having a structure according to Formula IV.

8. The photostabilizing compound of claim 1, wherein $R^1$ is selected from the group consisting of H, a straight or branched chain alkyl group having from about 1 to about 20 carbon atoms, and an alkoxy group having from about 1 to about 20 carbon atoms.

9. The photostabilizing compound of claim 1, wherein $R^1$ is selected from the group consisting of H, and a straight or branched chain alkyl selected from the group consisting of methyl, ethyl, propyl, butyl, 2-methyl-1-propyl, 2-methyl-2-propyl, pentyl, 2-methyl-2-butyl, hexyl, heptyl, octyl, decyl, or dodecyl.

10. The photostabilizing compound of claim 1, wherein $R^2$ is a straight or branched chain alkyl group having from about 1 to about 20 carbon atoms.

11. The photostabilizing compound of claim 10, wherein $R^2$ is a straight or branched chain alkyl group having at least 8, no more than 12 carbon atoms.

12. The photostabilizing compound of claim 11, wherein $R^2$ is a straight or branched chain alkyl group having 8 carbon atoms.

13. The photostabilizing compound of claim 1, wherein the photostabilizing compound is selected from the group consisting of:

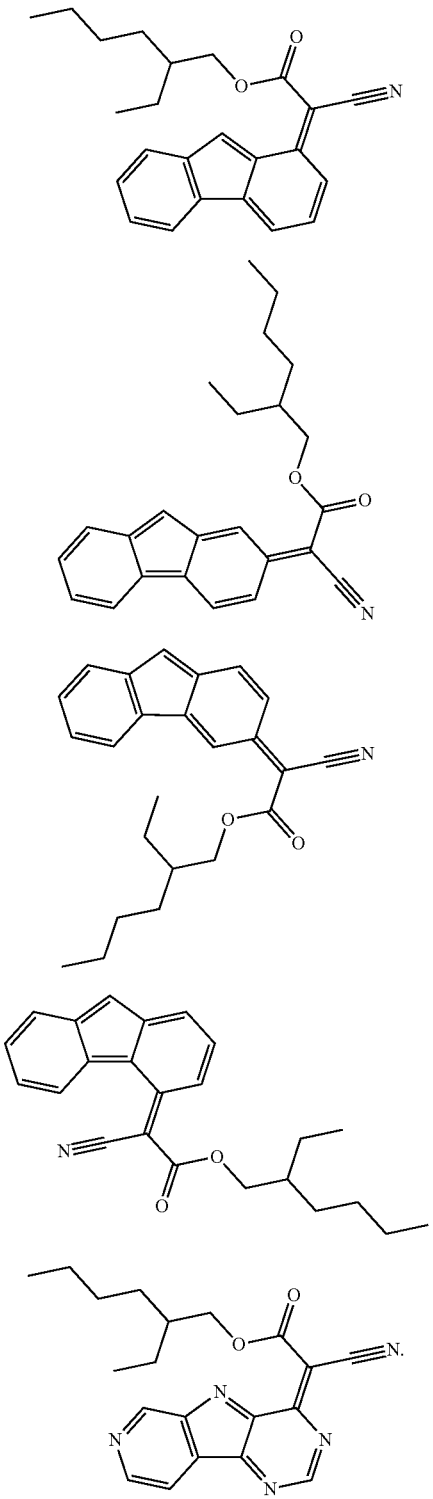

14. A composition comprising at least one photostabilizing compound having the structure according to the formula selected from the group consisting of:

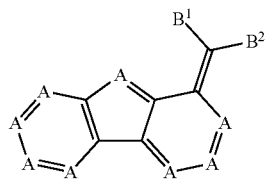

Formula I

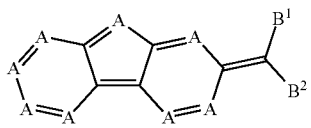

Formula II

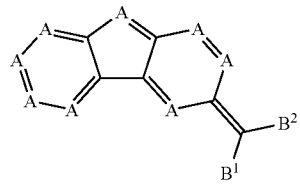

Formula III

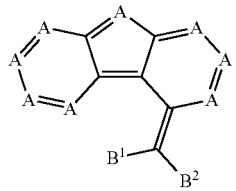

Formula IV wherein each A is independently selected from the group consisting of $CR^1$ and N;

wherein $R^1$ is selected from the group consisting of H, OH, a straight or branched chain alkyl group having from about 1 to about 20 carbon atoms, an alkoxy group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms;

wherein no more than four As are N;

Wherein each of $B^1$ and $B^2$ is independently selected from the group consisting of CN, $C(=O)OR^2$, with the proviso that $B^1$ and $B^2$ are not both CN;

wherein $R^2$ is selected from the group consisting of H, an alkyl group having from about 1 to about 20 carbon atoms, an alkenyl group having from about 2 to about 20 carbon atoms, an alkynyl group having from about 2 to about 20 carbon atoms, and an aryl group having from about 6 to about 20 carbon atoms.

15. The composition of claim 14, wherein the photostabilizing compound is present in amount ranging from 0.01 to 25% by weight of the total composition.

16. The composition of claim 14, further comprising at least one photoactive compound.

17. The composition of claim 16, wherein the photoactive compound is selected from the group consisting of a retinoid, a sunscreen, or mixture thereof.

18. The composition of claim 17, wherein the photoactive compound is a retinoid.

19. The composition of claim 18, wherein the retinoid is present in amount ranging from about 0.0001 to about 20% by weight of the total composition.

20. The composition of claim 17, wherein the photoactive compound is a sunscreen.

21. The composition of claim 20, wherein the sunscreen is selected from the group consisting of a UVA chemical sunscreen, a UVB chemical sunscreen, a physical sunscreen, and mixture thereof.

22. The composition of claim 21, wherein the sunscreen is a UVA chemical sunscreen.

23. The composition of claim 22, wherein the UVA chemical sunscreen is present in amount ranging from about 0.001 to about 20% by weight of the total composition.

24. The composition of claim 21, wherein the sunscreen is a UVB chemical sunscreen.

25. The composition of claim 24, wherein the UVB chemical sunscreen is present in amount ranging from about 0.001 to about 45% by weight of the total composition.

26. The composition of claim 16, further comprising at least one ingredient selected from the group consisting of oils, surfactants, humectants, botanical extracts, particulate materials, antioxidants, and other vitamins.

* * * * *